(12) United States Patent
Tonelli et al.

(10) Patent No.: US 7,781,170 B2
(45) Date of Patent: Aug. 24, 2010

(54) DETECTION OF ANALYTES IN FECAL SAMPLES

(75) Inventors: Quentin Tonelli, Portland, ME (US); Michael Monn, Falmouth, ME (US); Randall Groat, Falmouth, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

(21) Appl. No.: 10/424,282

(22) Filed: Apr. 25, 2003

(65) Prior Publication Data

US 2004/0214244 A1    Oct. 28, 2004

(51) Int. Cl.
G01N 33/53  (2006.01)
(52) U.S. Cl. ............... 435/7.1; 435/7.92; 435/7.93; 435/7.94; 436/518
(58) Field of Classification Search ............ 435/7.1, 435/7.92–7.95; 436/518, 535, 501, 524; 424/151.1
See application file for complete search history.

(56) References Cited

U.S. PATENT DOCUMENTS

| | | | | |
|---|---|---|---|---|
| 4,322,495 A | * | 3/1982 | Kato | 435/7.22 |
| 4,839,275 A | * | 6/1989 | Weil | 435/7.22 |
| 4,978,504 A | | 12/1990 | Nason | |
| 5,078,968 A | | 1/1992 | Nason | |
| 5,238,649 A | | 8/1993 | Nason | |
| 5,266,266 A | | 11/1993 | Nason | |
| 5,726,010 A | | 3/1998 | Clark | |
| 6,057,166 A | | 5/2000 | Childs | |
| 6,391,569 B1 | * | 5/2002 | Grieve et al. | 435/7.22 |
| 2002/0132270 A1 | | 9/2002 | Lee | |
| 2003/0129680 A1 | * | 7/2003 | O'Connor, Jr. | 435/7.32 |

FOREIGN PATENT DOCUMENTS

| | | | |
|---|---|---|---|
| WO | WO 98/12563 | * | 3/1998 |
| WO | 02075313 | | 9/2002 |

OTHER PUBLICATIONS

Deplazes et al, Detection of Taenia hydatigena Copro-Antigens by ELISA in Dogs, Veterinary parasitology, (May 1990) 36 (1-2) pp. 91-103.*

Deplazes et al., Detection of Taenia hydatigena Copro-Antigens by ELISA is Dogs, vol. 36, (1990), pp. 91-103.*
Ott et al, Demonstration of Both Immunologically Unique and Common Antigenic Determinants in Dirofilaria Immitis and Toxocara Canis Using Monoclonal Antibodies, Veterinary Immunology and Immunopathology, vol. 10, (1985), pp. 147-153.*
Voller et al., The Enzyme Linked Immunosorbent Assay, Diagnostic Horizons, vol. 2, No. 1, Feb. 1978, pp. 1-7.*
Memoranda, Parasite antigens, Bull. World Health Organ, vol. 52, 1975 pp. 237-249.*
Foreyt, William, J.; Veterinary Parasitology Reference Manual; Fifth Edition, 2001, ISBN 0-8138-2419-2.
Roberts, L.S., et al; Foundations of Parasitology, Fifth Edition, 1996, Library of Congress Catalog Card No. 94-72939, ISBN 0-687-26071-S.
IDEXX Laboratories Canine Paravovirus Antigen Test Kit package insert.
Abdel-Rahman, et al., "*Evaluation of a diagnostic monoclonal antibody-based capture enzyme-linked immunosorbent assay for detection of a 26- to 28-kd Fasciola hepatica coproantigen in cattle*", *AJVR*, vol. 53, No. 5, p. 533-537 (1998).
Martinez-Maya, et al., *Taeniosis and Detection of Antibodies against Cysticeri among Inhabitants of a Rural Community in Guerro State*, Mexico, Salud Publica de Mexico, vol. 45, No. 2, Mar. 2003, pp. 84-89.
Duménigo, et al., "*Kinetics of antibody-based antigen detection in serum and faeces of sheep experimentally infected with Fasciola hepatica*", *Veterinary Parasitology*, 86 (1999), 23-31.
Williard, et al. , "*Diagnosis of Aelurostrongylus abstrusus and Dirofilaria immitis infections in cats from a humane shelter*", *JAVMA*, vol. 192, No. 7, p. 913-916, 1988.
De Oliveira, et al., *IgM-ELISA for Diagnosis of Schistosomiasis Mansoin in Low Endemic Areas*, Cademos de Saude Publica/ Ministerio de Saude, Fandacao Oswaldo Cruz, En Cola Nacional de Saude Publica., vol. 19, No. 1, pp. 255-261, Jan. 2003.
Southworth, "*Exine Development in Gerbera Jamesonii (Asteraceae" Mutisieae*), Amer. J. Bot., 70(7):1038-1047, 1983.
Carleton, et al., "*Prevalence of Dirofilaria immitis and gastrointestinal helminthes in cats euthanized at animal control agencies in northwest Georgia*", *Vetemary Parasitology*, 119 (2004) 319-326.

* cited by examiner

*Primary Examiner*—Melanie Yu
*Assistant Examiner*—Gary W Counts
(74) *Attorney, Agent, or Firm*—McDonnell Boehnen Hulbert & Berghoff LLP

(57) ABSTRACT

A method for detecting a parasitic worm infection of the digestive tract of a mammal. The method includes detecting the binding of a worm antibody to a worm antigen present in the soluble portion of a fecal sample of infected mammals.

16 Claims, No Drawings

DETECTION OF ANALYTES IN FECAL SAMPLES

FIELD OF THE INVENTION

The invention is related to the detection of parasitic worm infections in animals. More specifically, the invention is related to a method for detecting digestive tract parasites in mammals by determining the presence of worm antigen in animal feces.

BACKGROUND OF THE INVENTION

Parasitic worm (helminth) infections are common in animals and, if not diagnosed and treated, can cause serious disease or death. Current methods for diagnosis of parasitic worm infections primarily involve microscopic examination of fecal samples, either directly in fecal smears or following concentration of ova and parasites by flotation in density media. These microscopic methods are time consuming and require specialized equipment. In addition, the accuracy of results of these methods is highly dependent upon the skill and expertise of the operator. Heartworm infections can be detected in blood samples using currently available tests, such as the SNAP® Heartworm Antigen Test (IDEXX Laboratories, Inc., Westbrook, Me.).

Stool handling is disagreeable and hazardous. Sanitary and inoffensive procedures for processing stool are awkward and often complex. Such procedures may include weighing, centrifuging and storing, and are difficult except in a clinical laboratory equipped with a suitable apparatus, protective equipment, and a skilled technician. Therefore, any reduction in the number of steps required to perform a fecal test and any reduction in contact between test operator and the test material is desirable. Clinical laboratories have been using the immunoassay methods for the detection of various viruses, bacteria and non-helminth parasites and organisms in feces. However, there remains a need for a simple immunoassay method for the detection of a parasitic worm infection in feces.

SUMMARY OF THE INVENTION

The invention provides for a method of detecting the presence or absence of a parasitic worm infection in an animal. The method includes contacting the soluble worm component of a fecal sample from the animal with a first antibody raised against a disrupted parasitic worm, and detecting the presence or absence of an antigen/antibody complex. The detection step may include providing a second antibody that binds to the antigen of the antigen/antibody complex, wherein the second antibody is the same as the first antibody. The first or second antibody may be attached to a label or a phase that is immiscible with the sample, such as a solid phase.

In various aspects of the invention, the disrupted parasitic worm is a heartworm, tapeworm, roundworm, hookworm, or whipworm.

In another aspect, the invention provides for a method of detecting the presence or absence of a parasitic worm antigen in animal feces. The method includes (a) forming a mixture comprising the soluble portion of a fecal sample and an antibody raised against the trichloroacetic acid soluble fraction of a disrupted parasitic worm that specifically binds a heartworm antigen; and (b) detecting whether the antibody specifically binds an antigen in the fecal sample.

In still another aspect of the invention, the invention provides for a method of detecting whether the digestive tract of an animal is infected with a parasitic worm. The method includes immobilizing a heartworm antibody on a solid phase, adding a soluble portion of a fecal sample from the animal to the solid phase, and detecting the binding of a parasitic worm antigen to the immobilized antibody. The detecting of the binding of the parasitic worm antigen to the immobilized antibody may include contacting the solid phase with a heartworm antibody conjugated to a label. The method may also include adding a heartworm antigen conjugated to a label to the solid phase after the addition of the soluble portion of the fecal sample and determining the presence, absence or amount of the binding of the labeled antigen to the antibody.

In yet another aspect, the invention provides for a method of detecting the presence or absence of an intestinal parasitic worm infection. The method includes:
(a) providing a lateral flow immunoassay device having a solid phase;
(b) providing a first antibody raised against a heartworm antigen;
(c) immobilizing the first antibody on the solid phase of the immunoassay device;
(d) providing a second, labeled antibody;
(e) providing a soluble fraction of a fecal sample;
(f) contacting the soluble fraction of the fecal sample with the second, labeled antibody;
(g) allowing the soluble fraction of the fecal sample and the second, labeled antibody to flow along the immunoassay device towards the immobilized first antibody; and
(h) determining the presence or absence of an intestinal parasite by observing a signal in the vicinity of the first, immobilized antibody.

DETAILED DESCRIPTION

The invention provides for a method of testing for a parasitic worm infection of the digestive tract of an animal. Detection of the infection is accomplished by detecting the binding of a soluble worm antigen present in an animal fecal sample to a worm antibody.

Parasitic worms that are detectable using the invention include heartworms, roundworms, whipworms, tapeworms and hookworms. Soluble worm antigen is any worm component present in the soluble fraction of a fecal sample that can specifically and stably bind to a worm antibody. The presence of the antigen in animal feces indicates that the digestive tract of the animal is infected with a parasitic worm.

Antibodies to worm antigen, such as a worm polyclonal antibody, can be prepared by administering to a vertebrate, such as, for example, a rabbit or chicken, the trichloroacetic acid (TCA) soluble fraction of a disrupted parasitic worm. Serum or eggs from the immunized animal are collected. Antibodies are purified from the plasma or eggs by, for example, precipitation with ammonium sulfate, followed by chromatography, such as affinity chromatography. Techniques for producing and processing a polyclonal antibody are known in the art.

In one aspect of the invention, the worm antibody is an antibody raised against a heartworm antigen thereby creating a heartworm antibody. Heartworm disease is caused by the filarial nematode *Dirofilaria Immitis* (*D. immitis*) and has worldwide distribution. Adult heartworms inhabit the blood and vascular tissue of mammals, including, for example, dogs, especially in the heart and adjacent blood vessels. *D. immitis* often interferes with heart functions and blood circulation and can damage other vital organs.

It has been found that the heartworm antibody can be used to detect soluble antigen of other species of worm in fecal samples. Similarly, it is expected that antibodies raised against the trichloroacetic acid fraction of other disrupted parasitic worms can be used to detect antigen of various other worm species in fecal samples.

Feces of any animal can be tested. Samples may be collected by any readily available means. Samples should be kept refrigerated until testing.

The worm antigen is found in the soluble portion of fecal samples. Fecal samples can be prepared by any means known in the art. In one aspect, the sample is swabbed using a collection device using a "Snap-Valve" available from Medical Packaging Corporation, Camarillo, Calif., as described in U.S. Pat. No. 5,266,266, which is incorporated by reference herein in its entirety. Briefly, the sample collection device includes a hollow swab shaft extending between a fibrous swab tip and a housing base defining a reagent chamber with a liquid reagent contained therein. The swab member may be manipulated quickly and easily while holding the base to collect a fecal specimen on the fibrous swab tip. The swab is placed in a specimen chamber. A break-off nib on a rear end of the swab shaft member permits reagent delivery from the reagent chamber through a hollow swab shaft to contact the specimen on the swab tip.

The break-off nib is disposed within the reagent chamber and normally prevents reagent flow into the swab shaft. Deformation of the housing base is effective to sever the nib from the swab shaft at a preformed score to open the rear end of the swab shaft and permit reagent flow from the reagent chamber through the swab shaft to the swab tip.

Fecal sample on the swab tip can thus be solubilized in the specimen chamber. In one aspect, the housing is flexible, such as on the end of an eye dropper, so that the liquid reagent can be drawn up through the hollow shaft of the swab by suction created by the housing. By repeatedly expelling from, and drawing liquid into, the hollow shaft and housing, the liquid reagents can be thoroughly mixed with the fecal sample collected on the fibrous tip of the swab. In addition, the swab tip functions as a filter such that most solid solid fecal matter is not draw into the shaft.

In addition, preparation of the fecal sample can be accomplished using any of the known methods in the art. For example the soluble portion of the sample can be collected using filtration, centrifugation, or simple mixing followed by gravimetric settling.

When antibodies raised against heartworm antigen are used in the method of present invention, there is a possibility that a test subject having heartworm infection, but no fecal parasitic infection, will have heartworm antigen in the soluble portion of a fecal sample. This can be due to antigen transfer into the digestive track through internal bleeding or other means. A second heartworm antigen test on a blood sample could be performed if the fecal sample is positive. A heartworm negative blood test would confirm fecal parasites. Alternatively, the blood sample can be tested first, followed by a fecal test if the blood sample is negative for heartworm antigen. A positive on either test would indicate parasitic worm infection.

In one aspect, the antibodies of the invention are antibody molecules that specifically and stably bind to a *D. immitis* antigen. These antibodies are obtained by immunizing a vertebrate with antigen. This antigen can be prepared by disrupting worms in an aqueous buffer solution, centrifuging to remove insoluble and particulate components, adding of trichloroacetic acid to a concentration of 15% w/v, centrifuging to remove insoluble components, dialyzing against an aqueous buffer solution and lyophilizing. This preparation is used to produce antibodies in mammals using standard methods (see, e.g., Harlow, E. and D. Lane, 1988, "Antibodies: A Laboratory manual", Cold Spring Harbor Laboratory, Cold Spring Harbor, N.Y., USA, ISBN 0-87969-314-2 pp 92-286).

An antibody or fragments thereof can be a polyclonal antibody, a monoclonal antibody, a single chain antibody (scFv), a chimeric antibody, or a fragment of an antibody. Fragments of antibodies are a portion of an intact antibody comprising the antigen binding site or variable region of an intact antibody, wherein the portion is free of the constant heavy chain domains of the Fc region of the intact antibody. Examples of antibody fragments include Fab, Fab', Fab'-SH, F(ab')$_2$ and F$_v$ fragments.

An antibody of the invention can be any antibody class, including for example, IgG, IgM, IgA, IgD and IgE. An antibody can be made in vivo in suitable laboratory animals or in vitro using recombinant DNA techniques. Means for preparing and characterizing antibodies are well know in the art. See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68(1992). For example, polyclonal antibodies can be produced by administering a polypeptide specific for *D. immitis* to an animal, such as a human or other primate, mouse, rat, rabbit, guinea pig, goat, pig, cow, sheep, donkey, chicken, or horse.

Once the antibodies of the invention have been prepared, the detection of parasitic worm in fecal samples can be accomplished using any readily available method known to those of skill in the art, for example, ELISA, western blot, immuno-fluorescent assay, radio-immuno assay, fluorescent polarization immunoassay and reversible flow chromatographic binding assay procedures. Methods and devices of the invention facilitate sandwich or competition-type specific binding assays. In the case of a sandwich assay, analyte capture reagents are immobilized in a reactive zone. Following binding of the sample analyte, the complex is reacted with labeled specific binding reagents (e.g., an enzyme-antibody conjugate) and analyte detected (e.g., upon reaction with substrate). In the case of a competition assay, analyte capture reagents are immobilized at the reactive zone and are contacted simultaneously with sample analyte and labeled analyte (e.g., an analyte-enzyme conjugate). The amount of label detected at the reactive zone is inversely proportional to the amount of analyte in the sample.

In one aspect, the invention includes a device for detecting the presence of a parasitic worm infection in an animal. The device includes an antibody or fragment thereof that specifically binds a worm antigen, for example, a *D. immitis* antigen, immobilized on a solid support at a distinct location. Detection of immunocomplexes on the solid support can be by any means known in the art.

Immobilization of one or more analyte capture reagents onto a device or solid support is performed so that an analyte capture reagent will not be washed away by wash procedures, and so that its binding to analytes in a test sample is unimpeded by the solid support or device surface. One or more analyte capture reagents can be attached to a surface by physical adsorption (i.e., without the use of chemical linkers) or by chemical binding (i.e., with the use of chemical linkers). Chemical binding can generate stronger attachment of specific binding substances on a surface and provide defined orientation and conformation of the surface-bound molecules.

Another embodiment of the invention provides a device that is suitable for a lateral flow assay. For example, a test sample is added to a flow matrix at a first region (a sample application zone). The test sample is carried in a fluid flow path by capillary action to a second region of the flow matrix where a particulate label capable of binding and forming a first complex with an analyte in the test sample. The particulate label can be a colored latex particle, dye sol, or gold sol conjugated to, for example, an antibody specific for a worm antigen. The first complex is carried to a third region of the flow matrix where an antibody that specifically binds a worm antigen is immobilized at a distinct location. A second complex is formed between an immobilized antibody or a polypeptide and a first complex. For example, a first complex comprising a gold sol particle and antibody specific for a worm antigen will specifically bind and form a second complex with an immobilized antibody specific for worm. The particulate label that is part of the second complex can be directly visualized.

In another aspect, the invention includes one or more labeled specific binding reagents that can be mixed with a test sample prior to application to a device for of the invention. In this case it is not necessary to have labeled specific binding reagents deposited and dried on a specific binding reagent pad in the device. A labeled specific binding reagent, whether added to a test sample or pre-deposited on the device, can be for example, a labeled antibody specific for *D. immitis*. For example, a *D. immitis*-specific antibody raised in a chicken conjugated with horseradish peroxidase can be used as a labeled specific binding reagent.

Any or all of the above embodiments can be provided as a kit. In one particular example, such a kit would include a device complete with specific binding reagents (e.g., a non-immobilized labeled specific binding reagent and an immobilized analyte capture reagent) and wash reagent, as well as detector reagent and positive and negative control reagents, if desired or appropriate. In addition, other additives can be included, such as stabilizers, buffers, and the like. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample.

U.S. Pat. No. 5,726,010, which is incorporated herein by reference in its entirety, describes an example of a lateral flow device useful in the present invention. A worm antibody can be an immobilized analyte capture reagent in a reaction zone (solid phase). A second analyte capture reagent, i.e. a second worm antibody, that has been conjugated to a label, can either be added to the sample before the sample is added to the device, or the second analyte capture reagent can be incorporated into the device. For example the labeled specific binding reagent can be deposited and dried on a fluid flow path that provides fluid communication between the sample application zone and the solid phase. Contact of the labeled specific binding reagent with the fluid sample results in dissolution of the labeled specific binging reagent.

The device may also include a liquid reagent is a that transports unbound material (e.g., unreacted fluid sample and unbound specific binding reagents) away from the reaction zone (solid phase). A liquid reagent can be a wash reagent and serve only to remove unbound material from the reaction zone, or it can include a detector reagent and serve to both remove unbound material and facilitate analyte detection. For example, in the case of a specific binding reagent conjugated to an enzyme, the detector reagent includes a substrate that produces a detectable signal upon reaction with the enzyme-antibody conjugate at the reactive zone. In the case of a labeled specific binding reagent conjugated to a radioactive, fluorescent, or light-absorbing molecule, the detector reagent acts merely as a wash solution facilitating detection of complex formation at the reactive zone by washing away unbound labeled reagent.

Two or more liquid reagents can be present in a device, for example, a device can comprise a liquid reagent that acts as a wash reagent and a liquid reagent that acts as a detector reagent and facilitates analyte detection.

A liquid reagent can further include a limited quantity of an "inhibitor", i.e., a substance that blocks the development of the detectable end product. A limited quantity is an amount of inhibitor sufficient to block end product development until most or all excess, unbound material is transported away from the second region, at which time detectable end product is produced.

To ensure proper operation, any of the devices described herein can further include various binding reagents immobilized at locations distinct from the analyte capture reagent(s). For example, an immunoreagent that recognizes a species-specific (e.g., canine specific) antibody portion of a labeled specific binding reagent or an enzyme portion of an enzyme-labeled reagent can be included as a positive control to assess the viability of the reagents within the device. For example, a positive control can comprise an anti-horseradish peroxidase antibody that has been raised in, for example, a goat or a mouse. Additionally, a reagent, e.g., an antibody isolated from a non-immune member of the species from which the antibody portion of the enzyme-antibody conjugate was derived can be included as a negative control to assess the specificity of immunocomplex formation.

Example

SNAP® device technology (IDEXX Laboratories, Inc., Westbrook, Me., USA) was used to provide a solid phase with reversible, chromatographic flow of sample, and automatic, sequential flow of wash and enzyme substrate solutions as described in U.S. Pat. No. 5,726,010.

Reagent Specifics. An antibody reagent raised to heartworm antigen was deposited to form a sample spot on the solid phase of the SNAP® device. A negative control reagent was deposited to form a negative control spot and a positive control reagent was deposited to form a positive control spot on the solid phase of the SNAP® device. An antibody reagent raised to *D. immitis* worm antigen was chemically conjugated to the enzyme horseradish peroxidase and provided in a solution consisting of a buffer, detergent, and animal serum components.

Fresh, unpreserved canine fecal samples were collected at a commercial kennel. Samples were stored refrigerated until testing.

Fecal material was sampled with a swab, mixed with the antibody-enzyme conjugate solution, and applied to the SNAP® device. Following a short incubation period, the device was activated and color developed on the sample spots to provide the test result. Color development on the positive control spot indicated the test was valid. Color development on the sample spot greater than color development on the negative control Spot indicated the presence of worm antigen in the fecal sample and was scored as a positive test result.

Reference Test Method—Fecal Flotation/Microscopic Examination. A sucrose flotation solution (specific gravity=1.27) was used to concentrate ova and parasites for microscopic examination. A fecal sample of 0.5-3.0 g was added to 5 ml of flotation solution and mixed thoroughly. Flotation solution was added to form a meniscus, and ova and parasites were collected on a glass cover slip for 15-45 minutes. The cover slip was then removed, placed on a glass slide, and examined using an Olympus CH-2 light microscope (Olympus Optical Co., Ltd., Tokyo, Japan). Ova and parasites were identified by size and morphology.

SNAP® test results and reference test results for 32 canine fecal samples are given in Table 1. Twenty five samples were positive for the presence of parasitic worms by the microscopic examination reference test method. Twenty of these samples (80%) were positive for worm antigen using the SNAP® immunoassay. Positive samples by both methods included samples containing roundworms, hookworms, and whipworms. Seven samples were negative for parasitic worms by microscopic examination and six of these (85%) were also negative for worm antigen by the SNAP® immunoassay. Resolution of the true parasitic worm status for the six samples giving discrepant results between test methods was not pursued.

Although various specific embodiments of the present invention have been described herein, it is to be understood that the invention is not limited to those precise embodiments and that various changes or modifications can be affected therein by one skilled in the art without departing from the scope and spirit of the invention.

TABLE 1

| Sample | Microscopic Examination | | SNAP ® Device |
| --- | --- | --- | --- |
| | Result | Parasitic Worms Identified | Immunoassay Result (Visual Examination) |
| 37172 | Positive | roundworms | Negative |
| 36986 | Positive | hookworms, whipworms | Positive |
| 36814 | Positive | whipworms | Negative |
| 37164 | Positive | roundworms, hookworms | Positive |
| 37174 | Positive | hookworms | Positive |
| 38000 | Positive | hookworms | Positive |
| 37138 | Positive | hookworms, whipworms | Positive |
| 37186 | Positive | hookworms | Positive |
| 37168 | Positive | hookworms | Positive |
| 37034 | Positive | whipworms | Positive |
| 36707 | Positive | roundworms | Positive |
| 37159 | Positive | hookworms | Positive |
| 36449 | Positive | roundworms | Positive |
| 36528 | Negative | none detected | Negative |
| 37100 | Negative | none detected | Positive |
| 36438 | Negative | none detected | Negative |
| 36409 | Negative | none detected | Negative |
| 36206 | Positive | hookworms | Positive |
| 37311 | Positive | hookworms, whipworms | Positive |
| 37327 | Positive | roundworms, hookworms | Positive |
| 37406 | Positive | roundworms, hookworms | Positive |
| 37522 | Positive | roundworms | Positive |
| 37549 | Positive | hookworms | Negative |
| 37532 | Positive | hookworms | Negative |
| 37241 | Positive | hookworms, whipworms | Positive |
| 37330 | Positive | roundworms | Positive |
| 37331 | Positive | roundworms | Positive |
| 37427 | Positive | roundworms, hookworms | Positive |
| 37524 | Positive | hookworms, whipworms | Negative |
| 37464 | Negative | none detected | Negative |
| 36283 | Negative | none detected | Negative |
| 37173 | Negative | none detected | Negative |

We claim:

1. A method for detecting the presence or absence of an intestinal roundworm, hookworm, or whipworm infection in an animal comprising:
contacting a soluble worm component of a fecal sample from the animal with a first antibody specific for a trichloroacetic acid soluble fraction of a disrupted heartworm, wherein the first antibody binds an intestinal roundworm antigen, a hookworm antigen, and a whipworm antigen thereby forming an antigen/antibody complex; and
detecting the presence or absence of the antigen/antibody complex thereby determining the presence or absence of a intestinal roundworm, hookworm, or whipworm infection in the animal.

2. The method of claim 1 wherein the step of detecting further comprises providing a second antibody that binds to the antigen of the antigen/antibody complex, wherein the second antibody is specific for a worm antigen, wherein the worm antigen is selected from the group consisting of intestinal roundworm antigen, hookworm antigen, and a whipworm antigen.

3. The method of claim 1 wherein the animal is canine or feline.

4. The method of claim 2, wherein the first or second antibody is attached to a phase that is immiscible with the sample.

5. The method of claim 4, wherein the phase is a solid phase.

6. The method of claim 2 wherein the first or second antibody is bound to a label.

7. The method of claim 6 wherein the label is an enzyme, a colloidal particle, a radionuclide or a fluorophore.

8. A method for detecting the presence or absence of a parasitic worm antigen in animal feces comprising:
(a) forming a mixture comprising a soluble portion of a fecal sample and an antibody specific for a trichloroacetic acid soluble fraction of a disrupted, heartworm wherein the antibody binds an intestinal roundworm antigen, a hookworm antigen, and a whipworm antigen;
(b) detecting whether the antibody binds an antigen in the fecal sample, wherein the antigen is selected from the group consisting of intestinal roundworm antigen, hookworm antigen, and whipworm antigen, thereby determining the presence or absence of a parasitic worm antigen in feces.

9. The method of claim 8, wherein the antibody is attached to a phase that is immiscible with the sample.

10. The method of claim 9, wherein the phase is a solid phase.

11. The method of claim 8 wherein the antibody is bound to a detectable moiety.

12. The method of claim 11, wherein the detectable moiety is an enzyme, a colloidal particle, a radionuclide or a fluorophore.

13. A method for detecting whether the digestive tract of an animal is infected with tapeworms, intestinal roundworms, hookworms, or whipworms comprising:
immobilizing antibody specific for a trichloroacetic acid soluble fraction of a disrupted heartworm on a solid phase, wherein the antibody binds a tapeworm antigen, an intestinal roundworm antigen, a hookworm antigen and a whipworm antigen;
adding a soluble portion of a fecal sample from the animal to the solid phase;
detecting the binding of a parasitic worm antigen to the immobilized antibody, wherein the parasitic worm antigen is one or more of a tapeworm antigen, an intestinal roundworm antigen, a hookworm antigen, or a whipworm antigen, thereby detecting whether the animal is infected with tapeworms, intestinal roundworms, hookworms, or whipworms.

14. The method of claim 13 wherein detecting the binding of the parasitic worm antigen to the immobilized antibody comprises contacting the solid phase with a worm antibody conjugated to a label.

15. The method of claim 13 further comprising adding a worm antigen conjugated to a label to the soluble portion of a fecal sample from the animal prior to addition to the solid phase and determining the presence, absence or amount of the binding of the labeled antigen to the antibody.

16. The method of claim 13, further comprising testing a blood sample from the mammal to detect the presence or absence of heartworm antigen in the blood sample.

* * * * *